United States Patent
Landon et al.

(10) Patent No.: US 11,344,409 B2
(45) Date of Patent: May 31, 2022

(54) SYSTEM AND METHOD FOR CRIMPING A PROSTHETIC VALVE

(71) Applicant: Edwards Lifesciences Corporation, Irvine, CA (US)

(72) Inventors: David Robert Landon, Costa Mesa, CA (US); Glen T. Rabito, Lake Forest, CA (US); Hieu Minh Luong, Westminster, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 138 days.

(21) Appl. No.: 16/851,959

(22) Filed: Apr. 17, 2020

(65) Prior Publication Data
US 2020/0237509 A1    Jul. 30, 2020

Related U.S. Application Data

(62) Division of application No. 15/487,881, filed on Apr. 14, 2017, now Pat. No. 10,639,147.

(60) Provisional application No. 62/354,371, filed on Jun. 24, 2016.

(51) Int. Cl.
*A61F 2/24* (2006.01)
*B21D 39/04* (2006.01)
*A61F 2/95* (2013.01)

(52) U.S. Cl.
CPC ......... *A61F 2/2418* (2013.01); *A61F 2/2412* (2013.01); *A61F 2/9525* (2020.05); *B21D 39/04* (2013.01); *A61F 2/2436* (2013.01); *A61F 2/9522* (2020.05); *A61F 2210/0014* (2013.01); *A61F 2250/0069* (2013.01)

(58) Field of Classification Search
CPC ..... A61F 2/9522; A61F 2/9525; A61F 2/9526
See application file for complete search history.

(56) References Cited

U.S. PATENT DOCUMENTS

| | | |
|---|---|---|
| 1,438,681 A | 12/1922 | Bath |
| 1,493,515 A | 5/1924 | Berthold |
| 2,079,498 A | 5/1937 | Douglas |
| 2,787,925 A | 4/1957 | Buchanan et al. |
| 2,974,367 A | 3/1961 | Doering et al. |
| 4,350,036 A | 9/1982 | Valente |
| 5,411,521 A | 5/1995 | Putnam et al. |
| 5,626,604 A | 5/1997 | Cottone, Jr. |
| 5,749,921 A | 5/1998 | Lenker et al. |

(Continued)

FOREIGN PATENT DOCUMENTS

WO    03047468 A1    6/2003

*Primary Examiner* — Jacob J Cigna
(74) *Attorney, Agent, or Firm* — Klarquist Sparkman, LLP

(57) ABSTRACT

Embodiments of a crimping device for crimping a radially expandable and compressible prosthetic valve are disclosed. A crimping device can comprise a housing configured to receive a prosthetic valve in a radially expanded state. The housing member can include a funnel segment and an outlet in communication with the funnel segment. The crimping device can further comprise an actuator rotatably coupled to the housing, wherein rotation of the actuator relative to the housing causes the prosthetic valve to move axially through the funnel segment such that at least a portion of the prosthetic valve compresses radially by engagement with the funnel segment and exits the crimping device via the outlet.

21 Claims, 12 Drawing Sheets

(56) References Cited

U.S. PATENT DOCUMENTS

| | | |
|---|---|---|
| 5,810,873 A | 9/1998 | Morales |
| 5,836,952 A | 11/1998 | Davis et al. |
| 5,913,871 A | 6/1999 | Werneth et al. |
| 5,992,000 A | 11/1999 | Humphrey et al. |
| 6,009,614 A | 1/2000 | Morales |
| 6,068,635 A * | 5/2000 | Gianotti .................... A61F 2/95 29/235 |
| 6,074,381 A | 6/2000 | Dinh et al. |
| 6,082,990 A | 7/2000 | Jackson et al. |
| 6,167,605 B1 | 1/2001 | Morales |
| 6,309,383 B1 | 10/2001 | Campbell et al. |
| 6,352,547 B1 | 3/2002 | Brown et al. |
| 6,360,577 B2 | 3/2002 | Austin |
| 6,387,117 B1 | 5/2002 | Arnold, Jr. et al. |
| 6,558,418 B2 | 5/2003 | Carpentier et al. |
| 6,618,921 B1 | 9/2003 | Thornton |
| 6,629,350 B2 | 10/2003 | Motsenbocker |
| 6,651,478 B1 | 11/2003 | Kokish |
| 6,682,553 B1 | 1/2004 | Webler, Jr. |
| 6,730,118 B2 | 5/2004 | Spenser et al. |
| 6,769,161 B2 | 8/2004 | Brown et al. |
| 6,823,576 B2 | 11/2004 | Austin |
| 6,840,081 B2 | 1/2005 | Kokish |
| 6,889,579 B1 | 5/2005 | Brown |
| 6,915,560 B2 | 7/2005 | Austin |
| 6,920,674 B2 | 7/2005 | Thornton |
| 6,925,847 B2 | 8/2005 | Motsenbocker |
| 6,931,899 B2 | 8/2005 | Goff et al. |
| 6,968,607 B2 | 11/2005 | Motsenbocker |
| 6,988,881 B2 | 1/2006 | Motsenbocker et al. |
| 7,010,953 B2 | 3/2006 | Stupecky |
| 7,021,114 B2 | 4/2006 | Perreault |
| 7,069,794 B2 | 7/2006 | Motsenbocker et al. |
| 7,096,554 B2 | 8/2006 | Austin et al. |
| 7,143,625 B2 | 12/2006 | Edin |
| 7,152,452 B2 | 12/2006 | Kokish |
| 7,207,204 B2 | 4/2007 | Weber et al. |
| 7,225,518 B2 | 6/2007 | Eidenschink et al. |
| 7,284,401 B2 | 10/2007 | Larson et al. |
| 7,389,670 B1 | 6/2008 | Kokish et al. |
| 7,415,861 B2 | 8/2008 | Sokel |
| 7,487,579 B2 | 2/2009 | Eidenschink et al. |
| 7,530,253 B2 | 5/2009 | Spenser et al. |
| 7,587,801 B2 | 9/2009 | Austin |
| 7,628,051 B1 | 12/2009 | Kokish et al. |
| 7,895,876 B2 | 3/2011 | Spenser et al. |
| 7,967,138 B2 | 6/2011 | Ryan et al. |
| 8,006,535 B2 | 8/2011 | Righini et al. |
| 8,042,373 B2 | 10/2011 | Stenzel |
| 8,112,857 B2 | 2/2012 | Voelkl |
| 8,312,614 B2 | 11/2012 | Sokel |
| 8,333,800 B2 | 12/2012 | Bruszewski et al. |
| 8,438,895 B2 | 5/2013 | Perreault et al. |
| 8,479,380 B2 | 7/2013 | Malewicz et al. |
| 8,640,521 B2 | 2/2014 | Righini et al. |
| 9,114,036 B2 * | 8/2015 | Davis ........................ A61F 2/95 |
| 9,155,619 B2 * | 10/2015 | Liu ........................ A61F 2/0095 |
| 9,192,738 B2 | 11/2015 | Golan et al. |
| 9,364,325 B2 * | 6/2016 | Alon ...................... A61F 2/2418 |
| 9,788,931 B2 * | 10/2017 | Giordano .............. A61F 2/0095 |
| 10,188,515 B2 * | 1/2019 | Duffy ...................... A61F 2/243 |
| 10,245,136 B2 * | 4/2019 | Ino ........................ A61F 2/0095 |
| 10,245,145 B2 | 4/2019 | Mantanus et al. |
| 10,918,473 B2 * | 2/2021 | Nir ........................ A61F 2/0095 |
| 10,973,635 B2 * | 4/2021 | Duffy .................... A61F 2/0095 |
| 2003/0192164 A1 | 10/2003 | Austin |
| 2006/0213049 A1 | 9/2006 | Serrano et al. |
| 2007/0056346 A1 | 3/2007 | Spenser et al. |
| 2007/0061009 A1 | 3/2007 | Spenser et al. |
| 2009/0043249 A1 | 2/2009 | Sokel |
| 2010/0049313 A1 * | 2/2010 | Alon ...................... A61F 2/2418 623/2.11 |
| 2010/0292780 A1 * | 11/2010 | Straubinger .......... A61F 2/9525 623/1.23 |
| 2012/0083874 A1 * | 4/2012 | Dale ...................... A61F 2/2427 623/2.11 |
| 2012/0239142 A1 | 9/2012 | Liu et al. |
| 2013/0030418 A1 | 1/2013 | Taft et al. |
| 2013/0190859 A1 * | 7/2013 | Hillukka ............... A61F 2/9525 623/2.11 |
| 2013/0218139 A1 | 8/2013 | Fargahi |
| 2014/0046428 A1 * | 2/2014 | Cragg ...................... A61F 2/954 623/1.12 |
| 2014/0144000 A1 * | 5/2014 | Creaven ................ A61F 2/9525 29/505 |
| 2014/0163670 A1 * | 6/2014 | Alon ...................... A61F 2/2439 623/2.11 |
| 2014/0331475 A1 * | 11/2014 | Duffy .................... A61F 2/9525 29/446 |
| 2015/0107078 A1 | 4/2015 | Jahn et al. |
| 2015/0297381 A1 * | 10/2015 | Essinger ................ A61F 2/2427 623/1.12 |
| 2015/0336150 A1 | 11/2015 | Peterson et al. |
| 2016/0184096 A1 * | 6/2016 | Maimon ................ B23P 19/04 72/292 |
| 2016/0228249 A1 | 8/2016 | Mantanus et al. |
| 2017/0189215 A1 | 7/2017 | Merlo et al. |
| 2019/0021834 A1 * | 1/2019 | Nir ........................ A61F 2/9525 |
| 2019/0053900 A1 | 2/2019 | Finn et al. |
| 2019/0133758 A1 * | 5/2019 | Duffy .................... B23P 11/005 |
| 2021/0169630 A1 * | 6/2021 | Nir ............................ A61F 2/24 |
| 2021/0290375 A1 * | 9/2021 | Duffy ........................ A61F 2/95 |

* cited by examiner

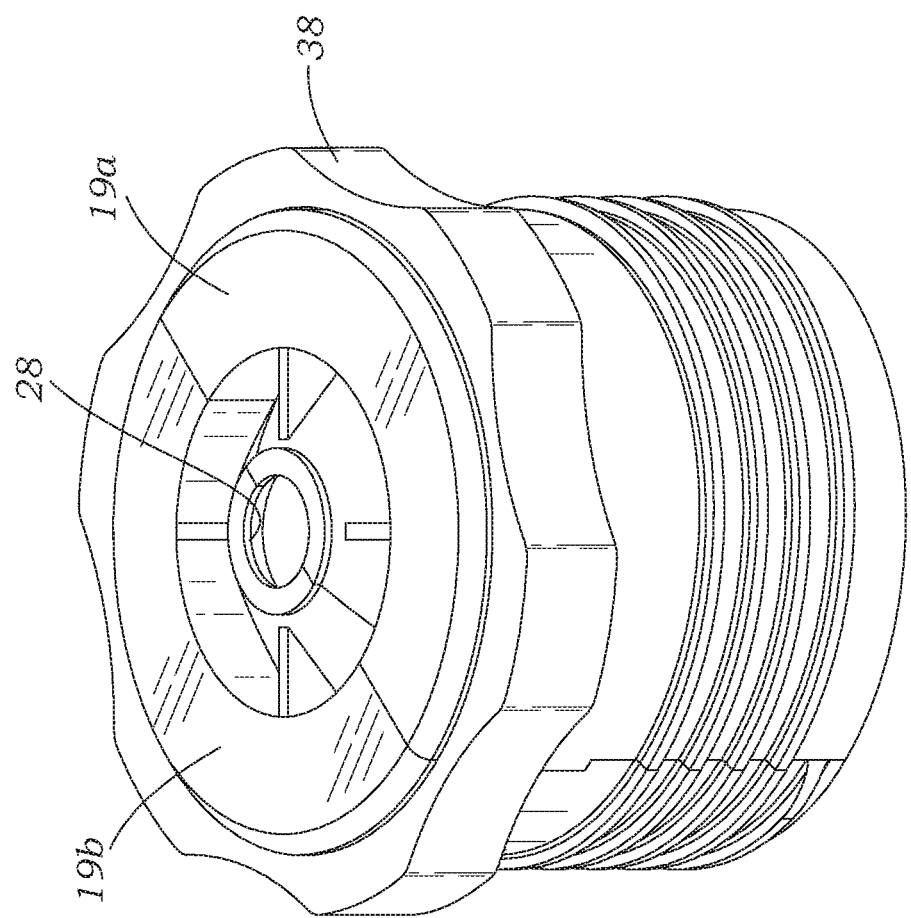

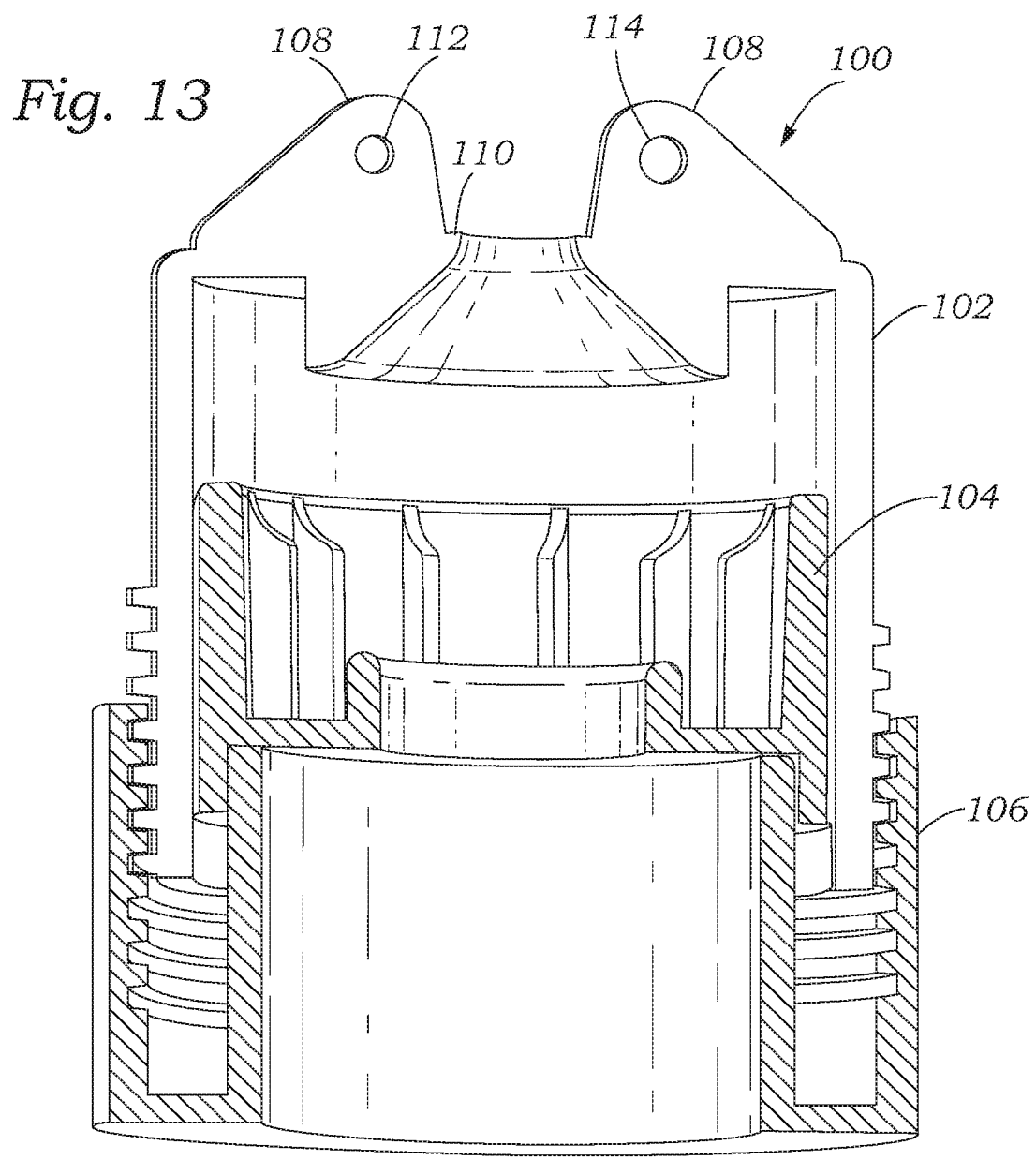

Fig. 14
Fig. 15
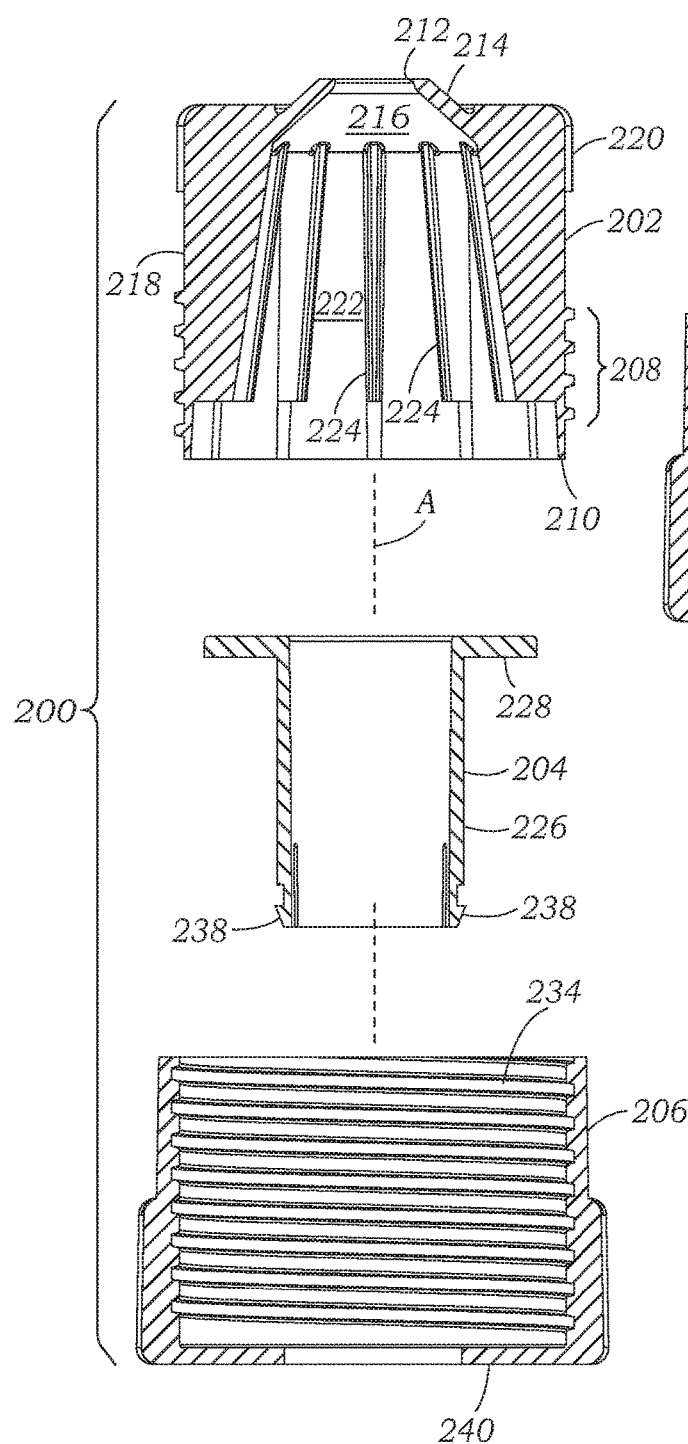
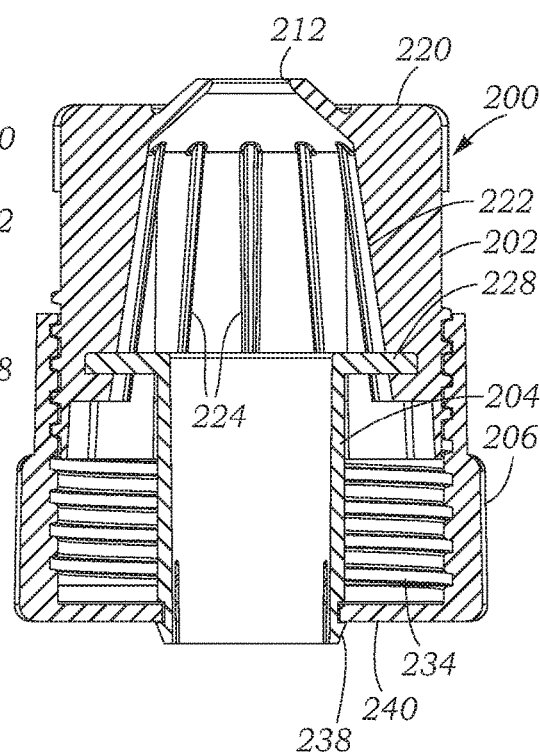

SYSTEM AND METHOD FOR CRIMPING A PROSTHETIC VALVE

CROSS REFERENCE TO RELATED APPLICATIONS

This application is a divisional of U.S. patent application Ser. No. 15/487,881, filed on Apr. 14, 2017, which claims the benefit of U.S. Provisional Application No. 62/354,371, filed Jun. 24, 2016. The prior applications are incorporated herein by reference in their entirety.

FIELD

This disclosure relates to systems and methods for crimping a prosthetic valve for delivery into a body.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled. The leaflets typically are made of biological materials such as pericardium valves or harvested valves. For improved function after deployment, it is often desirable to package and store such valves in the open (i.e., expanded) diameter inside a preserving solution up until the time the valve is mounted on a delivery device for implantation. Using this procedure, it may be necessary to crimp the valve in the operation room a few minutes before implantation, therefore precluding pre-crimping by the manufacturer. Thus many crimping devices are now shipped as a disposable accessory along with the valve and delivery system, thus increasing the importance of portability of such crimping devices.

Generally, conventional crimping devices operate by one of two methods. In one method, a stent is driven through a cone-like surface, which compresses the stent to a smaller diameter. For example, a static conical tube can be passed over a stent, thereby reducing its diameter. This method typically is used for crimping prosthetic valves having self-expanding metal frames (e.g., frames made of Nitinol), which are easily deformable. Self-expandable prosthetic valves typically are pushed from the conical tube of the crimping device into a sheath of a delivery apparatus, which retains the prosthetic valve in a radially compressed state. The second crimping method uses crimping jaws to create a cylinder-like surface that can change diameter. This method typically is used for crimping prosthetic valves having plastically-expandable frames (e.g., frames made of stainless steel or cobalt chromium alloys).

Self-expandable prosthetic valves typically have multiple connection features extending from the frame that form a releasable connection with the distal end of the delivery apparatus. Once the prosthetic valve has been deployed from the sheath inside the patient's body, the physician can release the connection between the delivery apparatus and the connection features of the prosthetic valve. A challenge in crimping self-expandable prosthetic valves involves the ability of the physician to easily and quickly crimp and load a prosthetic valve into a sheath of a delivery apparatus while aligning and connecting the connection features of the prosthetic with mating connection features of the delivery apparatus. There thus remains a need for an improved crimping device that addresses these and other disadvantages in the prior art.

SUMMARY

An exemplary embodiment of a crimping device for crimping a radially expandable and compressible prosthetic valve can include a housing configured to receive a prosthetic valve in a radially expanded state. The housing member can include a funnel segment and an outlet in communication with the funnel segment. The crimping device can further include an actuator rotatably coupled to the housing, wherein rotation of the actuator relative to the housing causes the prosthetic valve to move axially through the funnel segment such that at least a portion of the prosthetic valve compresses radially by engagement with the funnel segment and exits the crimping device via the outlet. Rotation of the actuator can cause the actuator to move axially over the housing.

Some embodiments of the crimping device can further comprise a pusher member configured to abut the prosthetic valve within the housing, wherein rotation of the actuator causes axial movement of the pusher member relative to the housing, thereby pushing the prosthetic valve through the housing. The pusher member can comprise an internal cavity, the internal cavity comprising a plurality of ribs configured to contact the prosthetic valve during radial compression. Additionally and/or alternatively, the pusher member can include an annular groove configured to receive an end portion of the prosthetic valve. The pusher member can be rotatably coupled to the actuator such that the actuator is rotatable relative to the pusher member. The pusher member can comprise releasable locking features for releasable engagement with the actuator.

In some embodiments of the crimping device, the housing can comprise two or more housing components that form a generally cylindrical shape when assembled to form the housing. A retaining member can be configured to releasably retain the two or more housing components together.

Additionally and/or alternatively, an exemplary crimping device for crimping a radially expandable and compressible prosthetic valve can comprise a housing having an outlet, the housing member configured to receive a prosthetic valve in a radially expanded state, and a pusher member that is axially movable relative to the housing, wherein the pusher member is configured to abut an end of the prosthetic valve and axial movement of the pusher member relative to the housing causes radial compression of the prosthetic valve and axial movement of the prosthetic valve through the outlet in a radially compressed, delivery configuration. The crimping device can further comprise an actuator that is rotatable relative to the housing and the pusher member to cause axial movement of the pusher member relative to the housing.

In some embodiments, an internal surface of the housing can include a plurality of ribs configured to receive a prosthetic valve in a radially expanded state. Additionally and/or alternatively, the pusher member can further include a plurality of fins disposed between the plurality of ribs and configured to slidingly engage the plurality of ribs during axial movement of the pusher member. The housing member can further comprise a tapered internal wall that terminates at the outlet. The internal wall can cause radial compression of the prosthetic valve during axial movement of the pusher member relative to the housing. In some embodiments, the pusher member can be rotatably coupled to the actuator such that the actuator is rotatable relative to the pusher member.

An exemplary method for crimping a prosthetic valve can comprise rotating an actuator of a crimping device relative to a housing of the crimping device, wherein the housing includes a funnel in communication with an outlet of the crimping device, and slidingly engaging the prosthetic valve with the funnel such that at least a portion of the prosthetic valve compresses radially and exits the crimping device via the outlet. In some embodiments, the method can further comprise advancing the prosthetic valve out of an outlet of the crimping device and into a sheath of a delivery apparatus.

In some embodiments, the funnel can comprise a plurality of ribs extending radially inward toward a longitudinal axis of the crimping device and the method for crimping can further comprise aligning at least a portion of a frame of the prosthetic valve within the plurality of ribs. The housing can comprise two or more housing components, wherein each housing component comprises a portion of the funnel. In some embodiments the method can further comprise assembling the two or more housing components and placing the housing co-axially around a delivery apparatus prior to crimping of the prosthetic valve. Additionally and/or alternatively, the method can comprise disassembling the two or more housing components and removing them from the delivery apparatus.

The foregoing and other objects, features, and advantages of the invention will become more apparent from the following detailed description, which proceeds with reference to the accompanying figures.

BRIEF DESCRIPTION OF THE DRAWINGS

FIG. 8 is a perspective view of a housing assembly of the crimping device of FIG. 1 comprising the components shown in FIGS. 5-7.

FIG. 13 is a cross-sectional view of a crimping device, according to another embodiment.

FIG. 14 is a cross-sectional, exploded view of a crimping device, according to another embodiment.

FIG. 15 is a cross-sectional, assembled view of the crimping device of FIG. 14.

DETAILED DESCRIPTION

For purposes of this description, certain aspects, advantages, and novel features of the embodiments of this disclosure are described herein. Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

Figure 1:
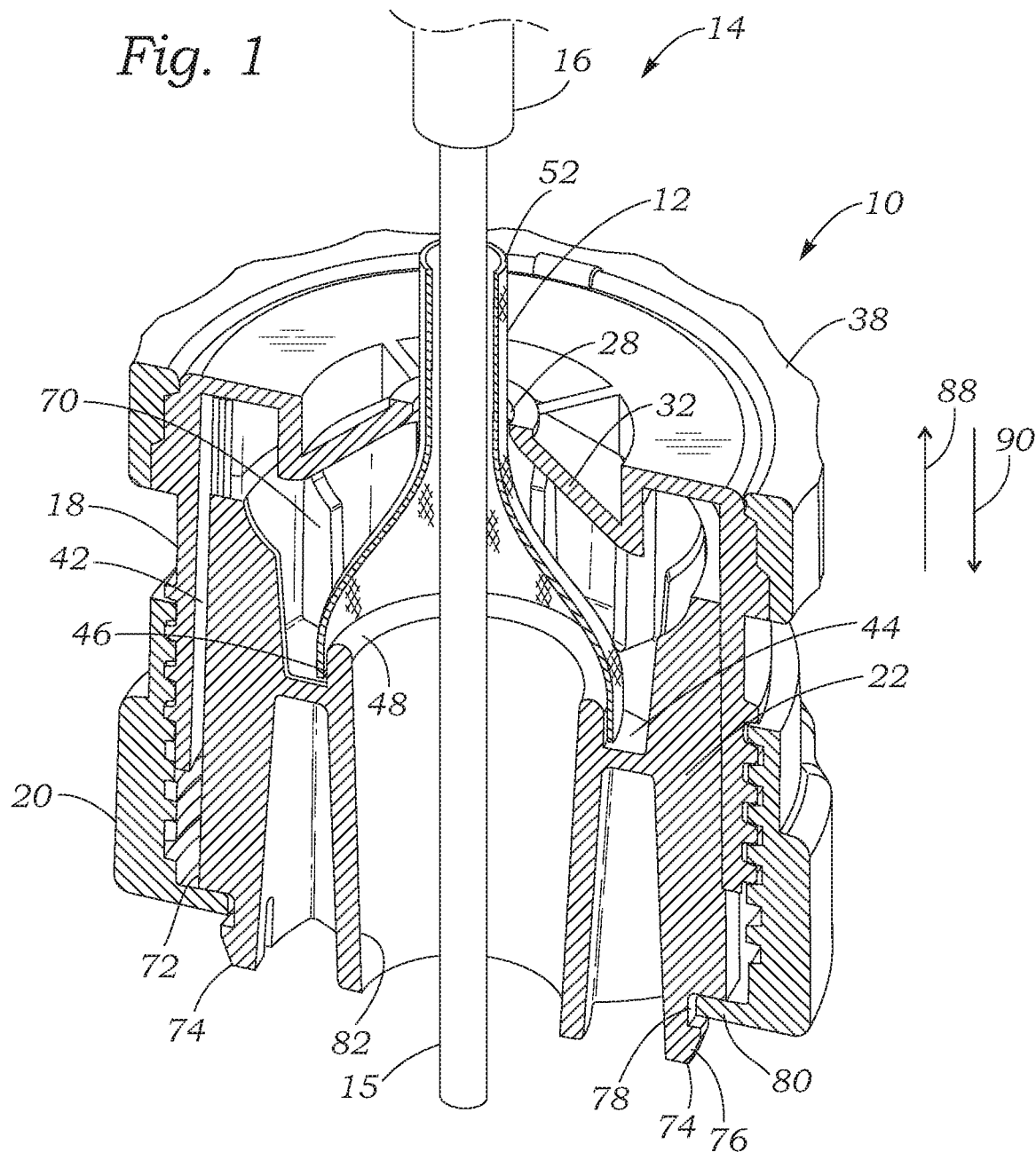
FIG. 1 is a cross-sectional view of an exemplary crimping device and a prosthetic valve shown being crimped and loaded onto a delivery apparatus.
Figure 20:
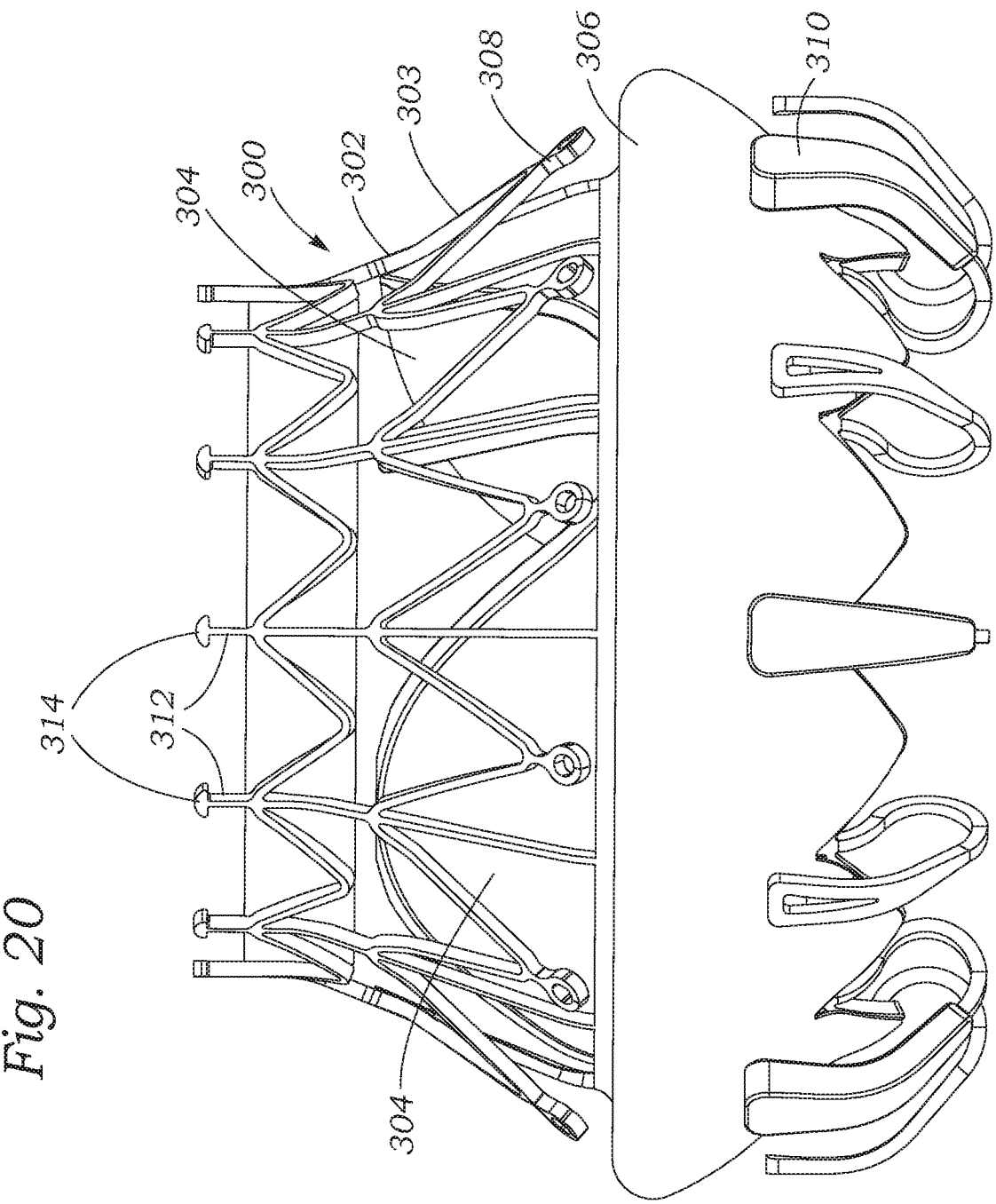
FIG. 20 is a side elevation view of an exemplary prosthetic valve that can be crimped using any of the crimping devices disclosed herein.

FIG. 1 shows an exemplary system for crimping a prosthetic valve and other crimpable, implantable medical devices, such as stents, grafts, etc. The illustrated system comprises a crimping device 10 and a radially expandable and compressible prosthetic valve 12, shown positioned within the crimping device 10. The crimping device 10 is configured to reduce the diameter of the prosthetic valve 12 from a fully expanded configuration to a radially compressed, delivery configuration for delivery into a patient. The prosthetic valve 12 is shown schematically in FIG. 1 for purposes of illustration. FIG. 20 is a more detailed illustration of an exemplary prosthetic valve that can be used with any of the crimping devices disclosed herein.

The exemplary system shown in FIG. 1 can further comprise a delivery apparatus 14 or a portion thereof. The delivery apparatus can comprise an inner shaft or catheter 15 and an outer sheath 16, which is sized to retain the prosthetic valve 12 in the radially compressed configuration for delivery into a patient. The prosthetic valve 12 can comprise any radially collapsible and expandable prosthetic valve, such as a prosthetic heart valve. The prosthetic valve 12 can be radially collapsible and expandable between an expanded configuration and a delivery configuration. The prosthetic valve 12 can be self-expandable or plastically expandable. A self-expandable valve can have a frame formed from a self-expanding metal (e.g., Nitinol). A plastically expandable valve can have a frame formed from a plastically deformable metal (e.g., stainless steel or cobalt chromium alloy).

After the prosthetic valve 12 is crimped onto the delivery apparatus 14 in the delivery configuration, the prosthetic valve 12 can be removed from the crimping device 10. In some embodiments, the prosthetic valve 12 and the delivery apparatus 14 can be advanced through an outlet of the crimping device 10 such that the crimping device 10 remains positioned around a portion of the delivery apparatus 14 that is distal to the prosthetic valve 12. In other embodiments, the crimping device 10 or components thereof can be configured to separate into pieces or open, such as like a clam shell, such that the crimping device 10 can be removed laterally from the delivery apparatus 14 and prosthetic valve 12, as further describe below. After the prosthetic valve 12 is removed from the crimping device 10, the prosthetic valve 12 and the delivery apparatus 14 can be introduced into a patient.

Figure 2:
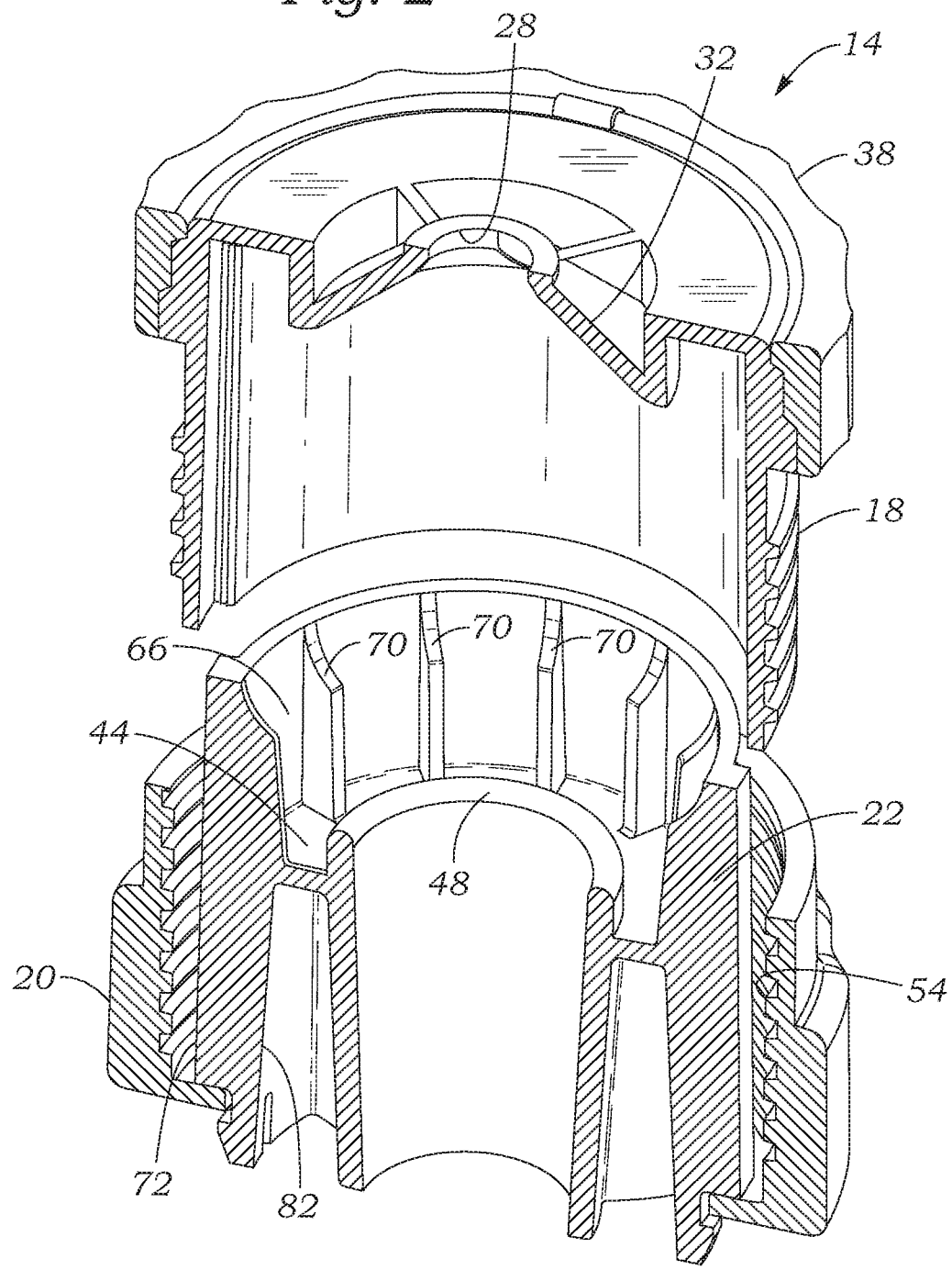
FIG. 2 is a cross-sectional, partially exploded view of the crimping device of FIG. 1.
Figure 5:
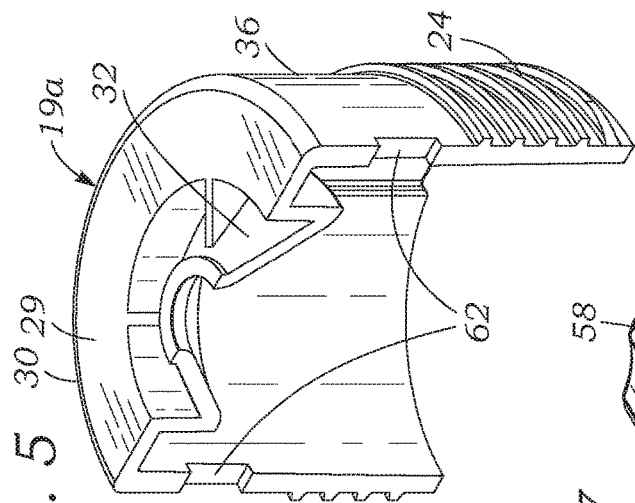
FIG. 5 is a perspective view of the housing component of FIG. 3.

As shown in FIG. 2, portions of the crimping device 10 can be removably coupled to each other, for example via a threaded engagement. For example, the crimping device 10 in the illustrated embodiment comprise a housing 18 threadably coupled to an actuator 20 in the form of a rotatable knob. The crimping device 10 can further comprise a pusher member or valve holder 22 (also referred to as a pedestal member 22) axially movable with respect to the housing member 18.

FIGS. 3-6 show the generally rigid housing 18 within which the prosthetic valve 12 can be positioned. The housing 18 in the illustrated embodiment comprises an assembly comprising first and second separable housing component 19a and 19b, respectively. Each housing component 19a, 19b can include an externally threaded portion 24 comprising external threads on an outer surface of the housing component adjacent a distal end 26, an outlet 28 at a proximal end 30, and an internal funnel segment 32. The funnel 32 segment of each housing component 19a, 19b comprises an internal tapered wall 34 that terminates at the outlet 28. For example, each funnel segment 32 can taper from a first, greater diameter adjacent an intermediate portion 36 of the housing component 19a, 19b to a second, smaller diameter adjacent the outlet 28. The diameter of the outlet 28 can be approximately the desired diameter of the prosthetic valve 12 in the radially compressed, delivery configuration. In some embodiments, the outlet 28 can be flush with an outer rim portion 29 at the proximal end 30 but in other embodiments the outlet 28 can be recessed with respect to or extend beyond the rim portion 29.

Figure 6:
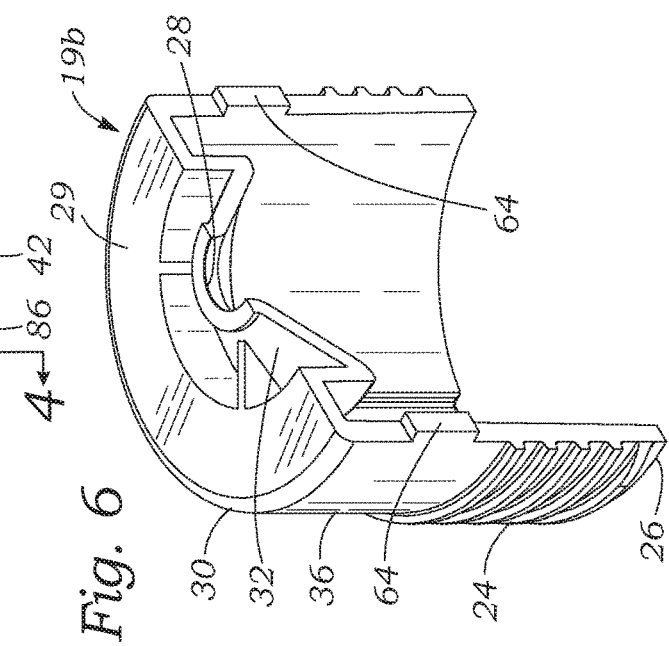
FIG. 6 is a perspective view of another housing component that is complimentary to the one shown in FIG. 5.
Figure 10:
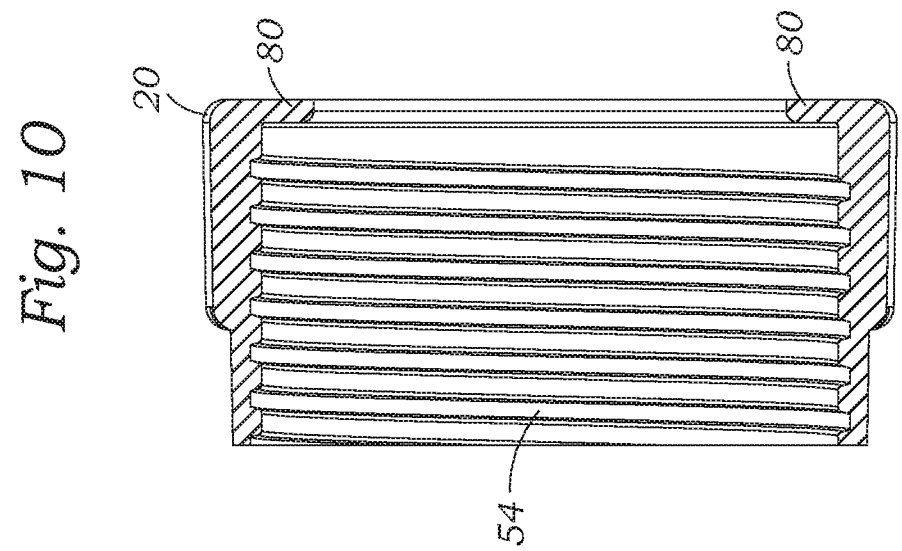
FIG. 10 is a cross-sectional view of the actuator of FIG. 9 taken alone line 10-10.
Figure 9:
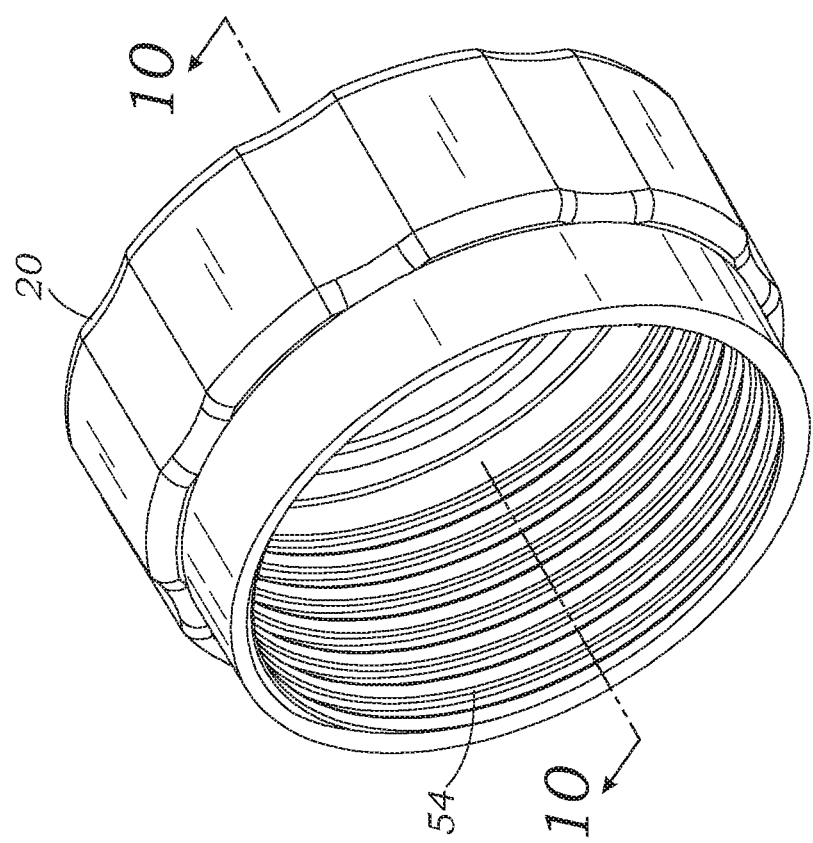
FIG. 9 is a perspective view of an actuator of the crimping device of FIG. 1.

Each housing component 19a, 19b can comprise a half cylinder. When placed together, the housing components 19a, 19b form a generally cylindrical or tubular shape. The housing components 19a, 19b can include mating features that assist the user in assembling the housing components 19a, 19b. In the illustrated embodiment, for example, the first housing component 19a has diametrically opposed recesses 62 formed in the longitudinal edges of the first housing component 19a (FIG. 5), while the second housing component 19b has diametrically opposed protrusions 64 formed in the longitudinal edges of the second housing component 19b (FIG. 6). The recesses 62 are sized to receive corresponding protrusions 64 when the housing components 19a, 19b are placed together.

In the assembled stated, the external threads 24 of the housing components 19a, 19b are aligned with each other to form continuous threads that extend around the outer surface of the housing assembly 18. The external threads of the housing assembly 18 are configured to mate with internal threads 54 of the actuator 20 to produce relative axial motion between the actuator 20 and the housing assembly 18 upon rotation of the actuator 20 relative to the housing assembly 18, as further described below.

Figure 7:
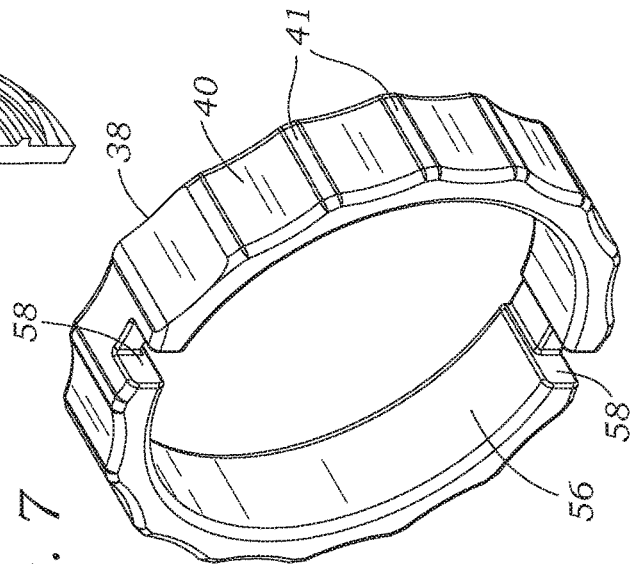
FIG. 7 is a perspective view of a retaining ring of the crimping device of FIG. 1.

The first and second housing components 19a, 19b can be held or locked together in the assembled state while a prosthetic valve is being crimped and then separated from each other to facilitate removal of the crimping device 10 from the delivery apparatus 14 after the prosthetic valve is loaded onto the delivery apparatus. For example, as shown in FIGS. 2 and 7, the crimping device 10 can further comprise a retaining member 38 (also referred to as a retaining ring) configured to encircle the housing components 19a, 19b, for example at their proximal ends 30, and releasably lock or retain the housing components 19a, 19b together. The retaining member 38 can include a gripping interface 40 for easy gripping and use by a user. The gripping interface 40 can include, for example, a plurality of circumferentially spaced ribs 41.

Figure 4:
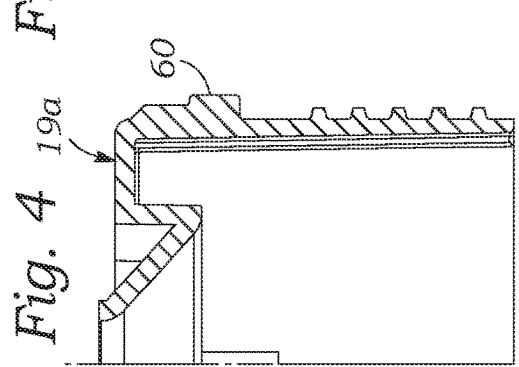
FIG. 4 is a cross-sectional view of the housing component of FIG. 3 taken along line 4-4 of FIG. 3.

The retaining member 38 can include an internal annular surface 56 that can be sized to slide over and form a frictional fit with the proximal end portions of the housing components 19a, 19b, such that retaining member can hold the housing components 19a, 19b together during use but can be easily removed from the housing components 19a, 19b by a user when it is desired to disassemble the housing assembly 18 and remove it from the delivery apparatus 14. The retaining member 38 can include one or more notches 58, such as two diametrically opposed notches 58 as shown in FIG. 7. The notches 58 can be configured to receive corresponding protrusions 60 extending from the outer surfaces of the housing components 19a, 19b to assist in retaining the retaining member 38 in place during use. FIG. 4 shows a protrusion 60 extending from the outer cylindrical surface of first housing component 19a. The second housing component 19b can include an identical protrusion 60 located diametrically opposed to the one on the first housing component 19a.

In certain embodiments, other techniques or mechanisms can be used to secure the retaining member 38 on the housing components 19a, 19b. For example, the notches 58 or other portions of the retaining member 38 can be configured to form a snap-fit connection with corresponding portions of the housing components 19a, 19b. Alternatively, the retaining member 38 can be have a threaded portion (e.g., internal threads) that engage corresponding threads (e.g., external threads) on the housing components 19a, 19b.

In alternative embodiments, the housing components 19a, 19b can include releasable, mating locking features that are configured engage each other and retain the housing components 19a, 19b in their assembled state without the use of a separate retaining member 38. For example, the first housing component 19a can have features that form a releasable snap-fit connection with corresponding mating features of the second housing component 19b.

In alternative embodiments, the housing assembly 18 can comprise a single cylindrical housing component or member rather than multiple, separable components. In such alternative embodiments, the retaining member 38 would not be required. In still alternative embodiments, the housing assembly 18 can comprise more than two housing components, for example, three, four, or more separable housing components that can be assembled into a cylindrical form.

As noted above, the crimping device 10 can further comprise an actuator 20 and a valve holder 22. The engagement of the inner threads 54 of the actuator 20 with the external threads 24 of the housing assembly 18 is such that rotation of the actuator 20 in one direction relative to the housing assembly 18 causes the actuator 20 to move proximally relative to the housing assembly 18 in the direction indicated by arrow 88 in FIG. 1. Rotation of the actuator 20 in the opposite direction causes the actuator 20 to move distally relative to the housing assembly 18 in the direction indicated by arrow 90 in FIG. 1.

As used herein, the term "proximal" or "proximally" means closer to or in a direction toward the user using the delivery apparatus 14. Thus, the proximal direction indicated by arrow 88 is toward a handle (not shown) of the delivery apparatus 14 and the user. As used herein, the term "distal" or "distally" means farther or in a direction away from the user using the delivery apparatus 14. Thus, the distal direction indicated by arrow 90 extends away from the handle of the delivery apparatus 14 and the user.

In the illustrated embodiment, the crimping device 10 is arranged on the delivery apparatus 14 at a location distal to the sheath 16 and such that the actuator 20 defines the distal end of the crimping device 10 and the retaining member 38 defines the proximal end of the crimping device 10. However, it should be understood that the crimping device 10 can be placed on the delivery apparatus 14 in a reverse position at a location proximal to a proximal opening of a sheath with the actuator 20 defining a proximal end of the crimping device 10 and the retaining member 38 defining the distal end of the crimping device 10. Thus, it can be appreciated that the terms "proximal" and "distal" when used to describe components of the crimping device and their operation, these terms are used as a matter of convenience and not require a certain orientation of the crimping device relative to the delivery apparatus or the user.

Figure 12:
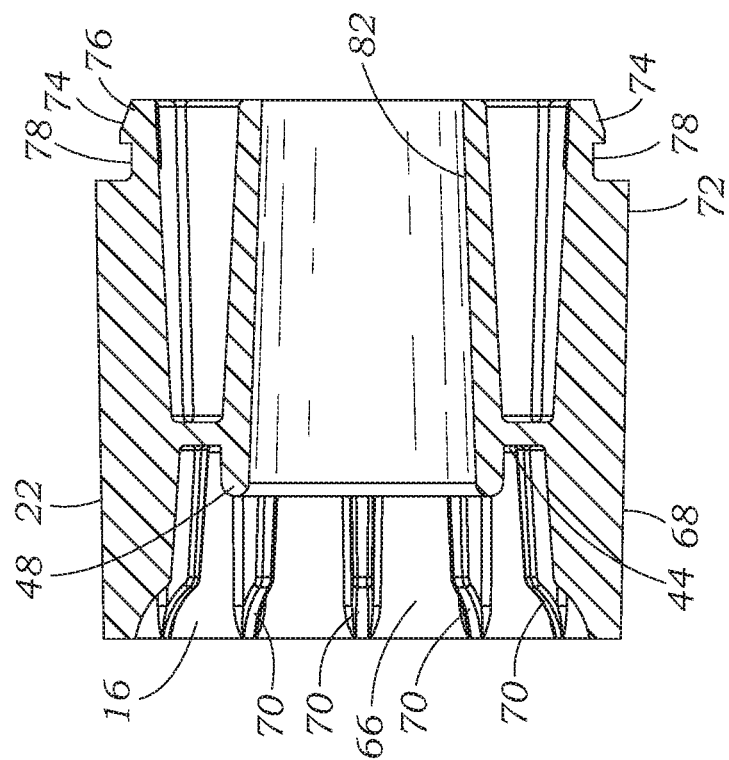
FIG. 12 is a cross-sectional view of the valve holder of FIG. 11 taken along line 12-12.
Figure 11:
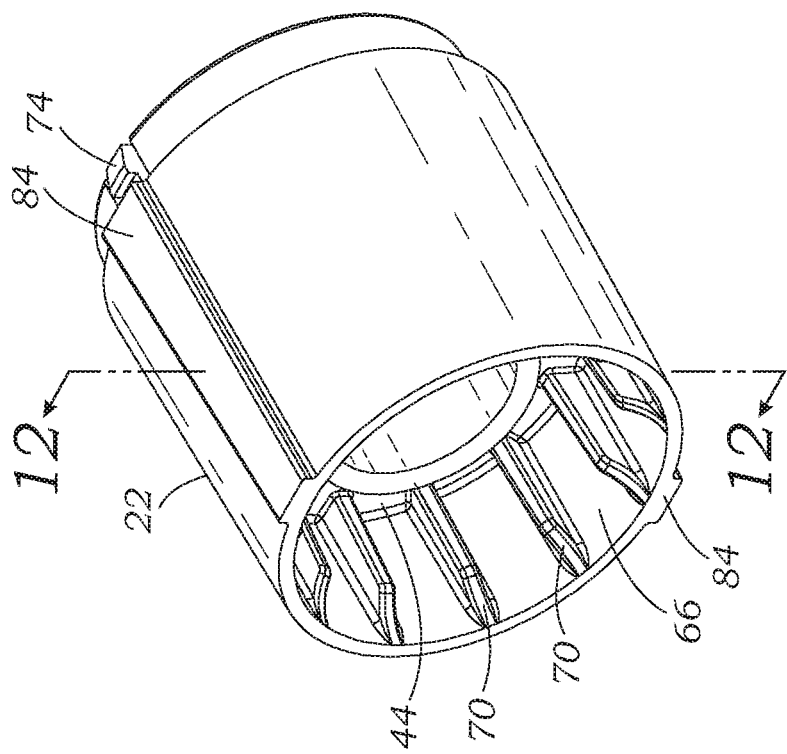
FIG. 11 is a perspective view of a valve holder of the crimping device of FIG. 1.

As best shown in FIGS. 11 and 12, the valve holder 22 can be generally cylindrical and sized to fit within an axially extending bore 42 of the housing assembly 18. The valve holder 22 is configured to hold at least a portion of the prosthetic valve 12 and push the prosthetic valve 12 axially through the bore 42 and the funnel segment 32 to effect crimping of the prosthetic valve 12. As shown, the valve holder 22 can comprise an internal annular recess 44 that is configured to engage, abut, or receive a first end portion 46 of the prosthetic valve 12. The annular recess 44 can include an annular lip 48 configured to hold the first end portion 46 of the prosthetic valve 12 within the recess 44.

The annular recess 44 can be in communication with a larger internal cavity or bore 66 formed within a proximal end portion 68 of the valve holder 22. The wall of the cavity 66 can be formed with a plurality of circumferentially spaced ribs 70 that extend longitudinally along and radially inwardly from the inner surface of the cavity 66. The ribs 70 can help support the prosthetic valve 12 such that there is less axial deformation of the prosthetic valve 12 during radial compression of the prosthetic valve 12. The ribs 70 can further assist in the proper placement of the prosthetic valve 12 in the crimping device 10. The number of plurality of ribs 70 can vary depending on the type and/or size of prosthetic valve to be crimped.

As further shown in FIGS. 1 and 12, a distal end portion 72 of the valve holder 22 can have an axially extending bore 82 that is in communication with the cavity 66 within the proximal end portion 68 of the valve holder. In this manner, the bore 82 and the cavity 66 form an axially extending passageway or lumen extending completely through the valve holder 22 to permit the delivery catheter 14 to be inserted through the valve holder 22.

The valve holder 22 can be rotatably coupled to the actuator 20 so as to permit rotation of the actuator 20 relative to the valve holder 22 and effect axial movement of the actuator 20 and the valve holder 22 relative to the housing assembly 18 upon rotation of the actuator. To such ends, the distal end portion 72 of the valve holder 22 can be formed with one or more releasable locking features 74 (e.g., two diametrically opposed locking features 74 in the illustrated embodiment) configured to releasably engage the actuator 20. For example, as best shown in FIG. 1, each locking feature 74 can comprise a deflectable lip 76 and a notch or groove 78 that is sized to receive an inwardly turned annular ledge 80 of the actuator 20. The lips 76 can be deflected inwardly when pressed against the ledge 80, which allows the ledge 80 to slide into the grooves 78, thereby forming a snap-fit connection between the ledge 80 and the locking features 74.

The grooves 78 can be slightly oversized relative to the ledge 80 to permit rotation of the ledge 80 within the grooves 78 upon rotation of the actuator 20 relative to the valve holder 22. Due to the threaded engagement of the actuator 20 and the housing assembly 18, rotation of the actuator 20 is effective to cause relative axial movement between the actuator 20 and the housing assembly 18. The ledge 80 in engagement with the grooves 78 transfers axial movement of the actuator 20 to the valve holder 22 such that axial movement of the actuator 20 is effective to move the valve holder 22 axially relative to the housing assembly 18 in the same direction. The valve holder 22 in turn pushes the prosthetic valve 12 axially though the housing assembly 18. Thus, rotation of the actuator 20 relative to the housing assembly 18 can urge the valve holder 22 against the first end 46 of the prosthetic valve 12 thereby forcing the prosthetic valve 12 against the tapered walls 34 of the funnel 32, thereby causing the prosthetic valve 12 to radially compress as it is pushed through the funnel 32 and outwardly through the outlet opening 28.

If desired, the actuator 20 can be removed from the valve holder 22 by pressing the lips 76 of the locking features inwardly past the radial innermost edge of the ledge 80, which allows the actuator 20 to be slid axially away from and out of engagement with the distal end portion 72 of the valve holder 22. In other embodiments, the actuator 20 need not be removable from the valve holder 22 and instead can be permanently coupled to the valve holder 22 but otherwise allows for relative rotation of the actuator 20 and the valve holder 22 as previously described above.

Figure 3:
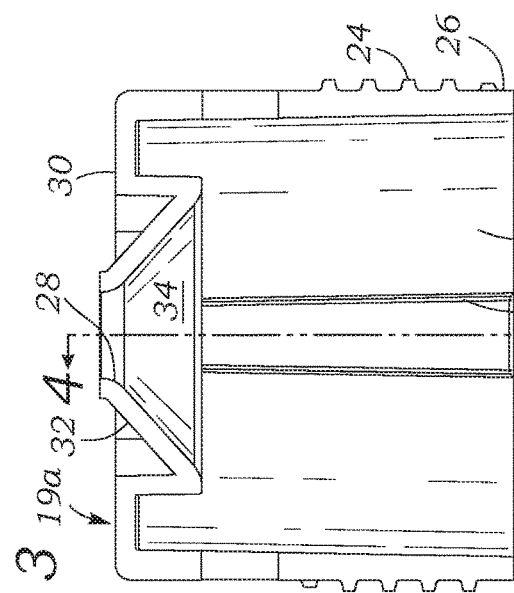
FIG. 3 is a side view of a housing component of the crimping device of FIG. 1.

As shown in FIG. 11, the valve holder 22 can have one or more longitudinally extending, external ribs or protrusions 84 (two diametrically opposed ribs 84 in the illustrated embodiment). The external ribs 84 are sized to be received in respective longitudinal slots 86 in each housing component 19a, 19b (see FIG. 3). Although only the slot 86 of the first housing component 19a is shown in FIG. 3, the second housing component 19b has an identical slot 86 diametrically opposed to the one in the first housing component 19a. The engagement of the ribs 84 within the slots 86 can be used to align the valve holder 22 within the housing assembly 18 and prevents any rotation of the valve holder 22 relative to the actuator 20 and the housing assembly 18 upon rotation of the actuator 20.

The threaded engagement of the actuator 20 and the housing assembly 18 can allow a user to precisely control the advancement of the prosthetic valve 12 out of the crimping device 10 and/or radial compression of the prosthetic valve 12. The crimping device 10 further allows for a one-person operation of the crimping device 10 and a repeatable, predictable procedure for crimping and loading a prosthetic valve 12. Some embodiments of the prosthetic valve 12 can include connection features that form a releasable connection with mating features of the delivery apparatus 14 (the connection features are located at the end of the prosthetic valve opposite the end in engagement with the valve holder 22) (e.g., see connecting arms 312 of prosthetic valve 300, described in further detail below). The connection features of the prosthetic valve have to be radially compressed while maintaining rotational alignment with the mating features of the delivery apparatus. The crimping device 10 allows a single operator to control crimping of the prosthetic valve while maintaining the rotational alignment of the connection features of the prosthetic valve with the mating features of the delivery apparatus. As the prosthetic valve is advanced out of the outlet 28 of the crimping device 10, the operator can connect the connection features of the prosthetic valve to the mating features of the delivery apparatus.

In the embodiment shown in FIG. 3, for example, the prosthetic valve 12 can be advanced through the outlet 28 of the crimping device 10 and into the sheath 16 of the delivery apparatus 14. The sheath 16 can be a tubular structure configured to contain the prosthetic valve 12 in the delivery configuration. The crimping device 10 can then be removed from the delivery apparatus 14 by sliding it distally off the inner shaft 15 (in the direction of arrow 90).

In some embodiments, the delivery apparatus 14 can include a nose cone or tip portion at the distal end of the inner shaft 15, which can prevent removal of the crimping device 10 by sliding it distally off the inner shaft 15. In such cases, the crimping device 10 can be disassembled by rotating the actuator 20 in the opposite direction to cause the actuator 20 to move distally relative to the housing assembly 18 (in the direction of arrow 90) until the actuator 20 is disengaged and removed from the housing assembly 18. The retaining member 38 can be slid off of the proximal end of the housing assembly 18, which then allows the first and second housing components 19a, 19b to be separated laterally away from each other and the delivery apparatus 14. The valve holder 22 desirably has a large enough lumen to be slid off the delivery apparatus 14, such as by sliding the valve holder 22 distally relative to the inner shaft 15 until it is removed from the distal end of the delivery apparatus.

The delivery apparatus 14 can then be inserted into the vasculature of a patient and used to deliver the prosthetic valve 12 percutaneously to the desired implantation location using conventional techniques. The distal end of the delivery apparatus 14 can be inserted into another device, such as an introducer sheath, which has been already inserted into a patient, to facilitate insertion of the delivery apparatus 14 into the patient.

In some embodiments, a system comprising a crimping device 10, a delivery apparatus 14, and a prosthetic valve 12 can be packaged and shipped from the manufacturer to the end user with the prosthetic valve 12 pre-loaded inside of the fully assembled crimping device 10 coaxially mounted on the delivery apparatus. In some embodiments, the system can further comprise a sterile package enclosing the crimping device 10 mounted on the distal end portion of the delivery apparatus, the prosthetic valve 12 pre-loaded in the crimping device, and the entire the delivery apparatus 14 or just the distal end portion of the delivery apparatus on which the crimping device and the prosthetic valve are mounted. In other embodiments, the system can further comprise another device, such as an introducer sheath, to assist in inserting the delivery apparatus 14 into a patient once the prosthetic valve has been loaded into the sheath 16.

In some embodiments, the prosthetic valve 12 can be in a partially crimped configuration prior to being assembled within the crimping device 10. For example, the prosthetic valve 12 can be pre-crimped to the partially crimped configuration using another crimping instrument, prior to being assembled into crimping device 10. In the partially crimped configuration, the prosthetic valve 12 has an outer diameter that is between that of the expanded configuration and that of the delivery configuration. In some embodiments, the prosthetic valve 12 can have an outer diameter in the partially crimped configuration that is closer to the outer diameter in the delivery configuration than to the outer diameter in the expanded configuration. For example, the prosthetic valve 12 in the partially crimped configuration can be crimped about 75% of the way from the expanded configuration to the delivery configuration. The crimping device 10 can also be configured to crimp the prosthetic valve 12 to the delivery configuration from the expanded configuration without first pre-crimping the prosthetic valve 12 to an intermediate partially crimped configuration.

FIG. 13 shows an alternative embodiment of a crimping device 100 comprising a housing, a valve holder or pusher member 104 and an actuator or knob 106. The housing can comprise a unitary, generally cylindrical structure. Alternatively, the housing can comprise or two or more separable housing components as described above. For example, the housing can include a first housing component 102 and a second housing component (not shown). When assembled together, the first housing component 102 and the second housing component can form a generally cylindrical or tubular shape. Both the first and the second housing components can include releasable, mating locking features that are configured to engage each other and retain the housing components in their assembled state. For example, each housing component can include one or more fins 108 extending from the proximal end of the housing component (shown on the first housing component 102 in FIG. 13), for example two such fins 108 on diametrically opposed sides of an outlet 110. One of the fins 108 on the first housing component 102 can include a threaded hole 112 and the other fin 108 can include a non-threaded hole 114. The non-threaded 114 hole may have a larger diameter of the threaded hole 112. The threaded hole 112 can be configured to align up with a non-threaded hole on a fin of the second housing component and the non-threaded hole 114 can be configured to align with a threaded hole on a fin of the second housing component (not shown). A threaded screw or knob (not shown) can be passed through first a non-threaded hole and then through the threaded hole of the first and second housing components to join and releasably retain the first and second housing components together.

FIGS. 14-19 show an alternative embodiment of a crimping device 200 comprising a housing 202, a valve holder or pusher member 204 and a rotatable actuator or knob 206. FIG. 14 is an exploded view of the crimping device 200. FIG. 15 is a cross-sectional, assembled view of the crimping device 200. The housing 202 can have a generally cylindrical shape having an externally threaded portion 208 along a distal end portion 210 and a funnel segment 214 along a proximal end portion 220 in communication with an outlet opening 212. In the illustrated embodiment, the housing 202 comprises a unitary, generally cylindrical structure. However, in other embodiments, the housing can comprise an assembly of a plurality of separable housing components, as described above in connection with the crimping device 10.

The funnel segment 214 comprises a conical or funnel shaped wall 216 that is tapered from a first, greater diameter adjacent an intermediate portion 218 of the housing 202 to a second, smaller diameter at the outlet 212. The housing 202 can further comprise internal tapered wall 222 extending from the distal end portion 210 of the housing 202 to approximately adjacent the distal end of the funnel segment 214. The internal tapered wall 222 tapers from a first larger diameter to a second, smaller diameter moving in a direction from the distal end portion 210 to the proximal end portion 220. In the illustrated embodiment, the wall 222 is tapered at a smaller angle relative to a longitudinal axis A of the crimping device than the funnel segment, which is tapered at a steeper angle relative to the longitudinal axis A. In other embodiments, the wall 222 can be tapered at the same angle as the funnel segment 214, or at a greater angle than the funnel segment 214.

The wall 222 can include a plurality of circumferentially spaced ribs 224 extending longitudinally along a portion or the entire length of the wall 222 and radially inwardly extending toward the longitudinal axis A. The width of the ribs (the width being the dimension extending from the wall 222 toward the longitudinal axis A) can increase along their length from a smaller width adjacent the distal end portion 210 to a greater width adjacent the proximal end portion 220. The ribs 224 function to prevent or at least minimize axial deformation of a prosthetic valve 250 (see FIG. 19) during radial compression and/or assist in alignment of the connection features of the prosthetic valve with mating features of the delivery apparatus.

In particular embodiments, the ribs 224 can also begin to radial compress a prosthetic valve 250 from the fully expanded diameter to a partially crimped diameter before it enters the funnel segment 214 where it is then crimped from the partially crimped diameter to the fully crimped diameter for loading into a delivery apparatus. Thus, in this manner, the housing 202 can have two crimping sections that can crimp the prosthetic valve at different rates due to the different tapering angles of the two sections. In the illustrated embodiment, for example, the wall 222 and the ribs 224 are tapered at a smaller angle relative to the longitudinal axis A than is the funnel segment 214, in which case the first crimping section (defined by the ribs 224) initially crimps the prosthetic valve a first amount and then is further crimped by the second crimping section (defined by the funnel segment 214) a second amount greater than the first amount.

Figure 17:
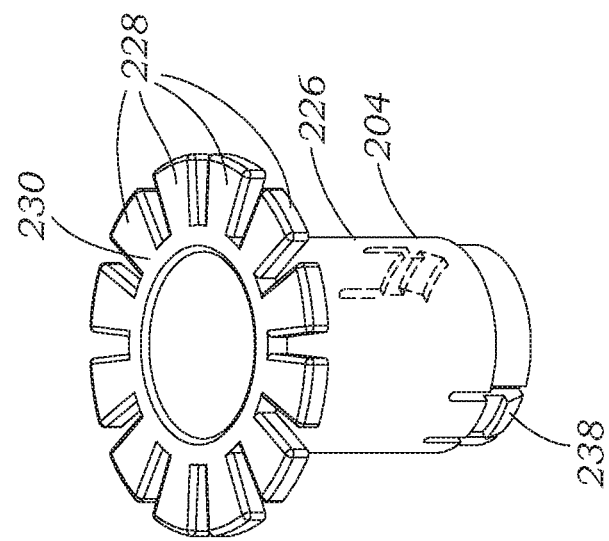
FIG. 17 is a top perspective view of a pusher member of the crimping device of FIG. 14.
Figure 16:
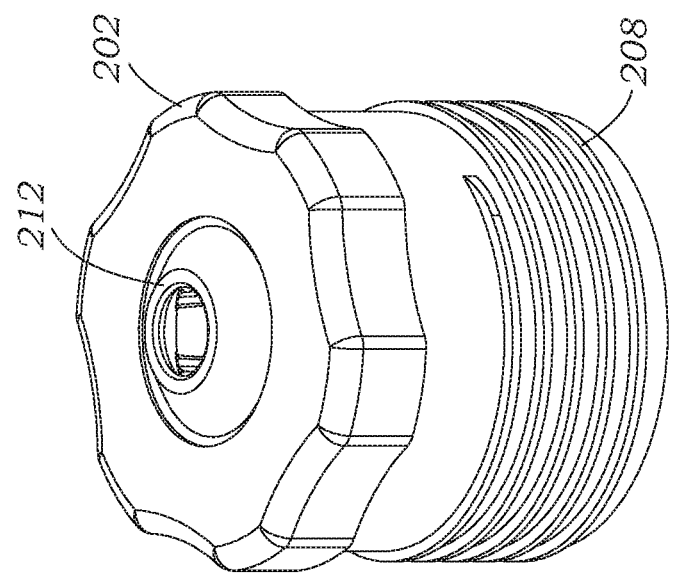
FIG. 16 is a top perspective view of a housing of the crimping device of FIG. 14.
Figure 18:
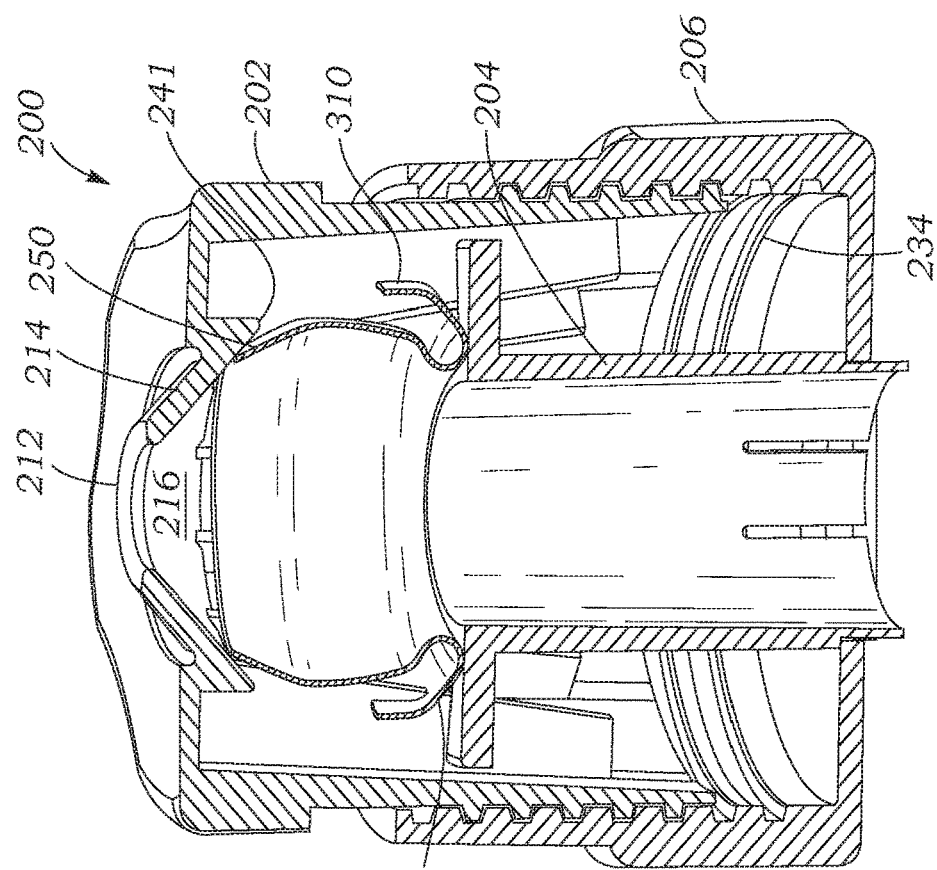
FIG. 18 is a cross-sectional perspective view of the crimping device of FIG. 14.

As best shown in FIG. 17, the pusher member 204 can comprise a generally cylindrical or tubular main body 226, an annular ledge 230 at the proximal end of the main body, and a plurality of circumferentially spaced, radially extending fins 228 extending from the ledge 230. The fins 228 can be configured to be slidably disposed between the ribs 224 of the housing 202 such that as the pusher member 204 moves axially with respect to the housing 202, the fins 228 slide between the ribs 224. Each of the fins 228 can have the shape of an angular segment that flares or widens in width extending in a radial direction away from the annular ledge 230 so as to generally correspond to the shape of the spaces between the ribs 224, as best shown in FIG. 18. The annular ledge 230 is configured to abut an adjacent end 232 of the prosthetic valve 250 when pushing the prosthetic valve through the housing 202.

In alternative embodiments, the pusher member 204 can have an annular recess (similar to the recess 44 of the valve holder 22) or a similar feature that is configured to hold or retain an end portion of a prosthetic valve as it is pushed through the housing 202.

The actuator 206 can have internal threads 234 configured to engage the external threads 208 of the housing 202 such that rotation of the actuator 206 causes the actuator 206 to move axially along the length of the housing 202. The actuator 206 can surround the pusher member 204 and can be coupled to the pusher member 204 such that axial movement of the actuator 206 (through rotation of the actuator 206 relative to the pusher member 204 and the housing 202) causes corresponding axial movement of the pusher member 204 through the housing 202. For example, the main body of the pusher member 204 can be formed with resilient locking features 238 configured to form a snap fit connection with an inwardly turned radial ledge 240 of the actuator 206.

The crimping device 200 can be used to crimp a prosthetic valve 250 in the manner described above in connection with the crimping device 10. Briefly, the prosthetic valve 250 can be inserted into the housing 202. The pusher member 204 (which can be preassembled to the actuator 206) is inserted into the housing 202 so as to engage an adjacent end 232 of the prosthetic valve 250 while the actuator 206 is screwed onto the outside of the housing 202. Although not shown, the housing 202, the prosthetic valve 250, the pusher member 204, and the actuator 206 can be positioned co-axially around the shaft of a delivery apparatus. As the actuator 206 is rotated relative to the housing 202, the actuator 206 moves axially along the housing 202, pushing the pusher member 204 through the housing 202, which in turn pushes the prosthetic valve 250 through the housing 202. As prosthetic valve 250 is pushed through the tapered wall segment 222 and the funnel segment 214, the prosthetic valve is radially compressed and pushed outwardly through the outlet 212. In particular embodiments, the prosthetic valve 250 can be pushed directly from the crimping device 200 into a sheath of a delivery apparatus (not shown).

FIG. 20 is a side elevation view of an exemplary prosthetic valve 300 that can be crimped using any of the crimping devices disclosed herein. The prosthetic valve 300 comprises a radially expandable and compressible metal frame 302 supporting a plurality of leaflets 304 inside of the frame. The prosthetic valve 300 can also include a sealing member 306 (e.g., a fabric skirt) secured on the outside of the frame 302 and configured to create a seal against a native valve annulus. In certain embodiments, the prosthetic valve 300 is self-expandable with the frame 302 being formed from a self-expanding metal (e.g., Nitinol).

The frame 302 can comprise a main body 303 and a first set of anchors 308 and a second set of anchors 310 extending toward each other from opposing portions of the main body 303. In particular embodiments, the prosthetic valve 300 is a prosthetic mitral valve and the anchors 308 are configured to help anchor the prosthetic valve 300 in the left atrium and the anchors 310 are configured to help anchor the prosthetic valve 300 in the left ventricle. The end of the frame 302 opposite the anchors 310 can include a plurality of connecting arms 312 having enlarged end portions 314. The end portions 314 are configured to engage mating features of a delivery apparatus to form a releasable connection between the prosthetic valve and the delivery apparatus.

Figure 19:
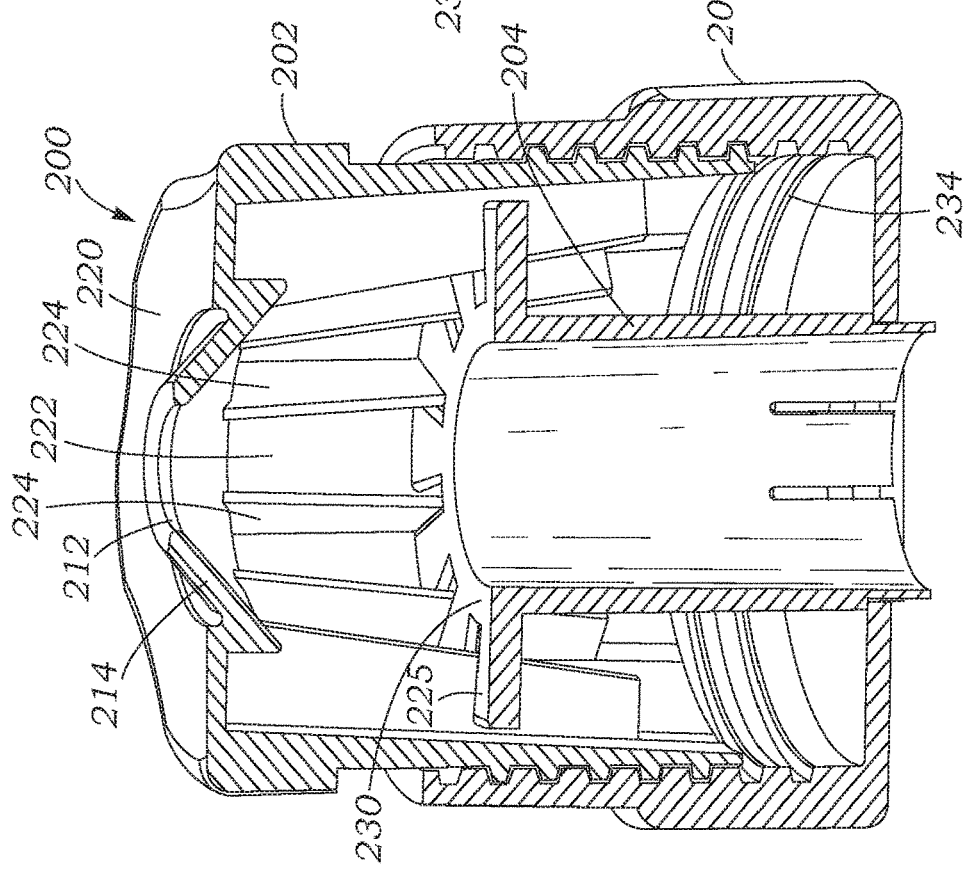
FIG. 19 is a cross-sectional perspective view of the crimping device of FIG. 14 and a prosthetic valve being crimped by the crimping device.

As noted above, the plurality of ribs 224 can aid in the alignment of the prosthetic valve 300. For example, the prosthetic valve 300 can be aligned within the crimping device such that one or both of the first and second set of anchors 308 and 310 are disposed between the plurality of ribs (as shown in FIG. 19 with respect to the second set of anchors 310), thereby ensuring that the enlarged end portions 314 are positioned for engagement with the mating features of the delivery apparatus to form a releasable connection between the prosthetic valve and the delivery apparatus. As the prosthetic valve is pushed out of the outlet 212, the second set of anchors 310 can be radially compressed against the main body 303 of the frame 302 of the prosthetic valve 300. In alternative embodiments, the leading end 241 (FIG. 19) of the funnel segment 214 can be adapted to cause the anchors 310 to bend away from the main body 303 into a substantially straightened configuration extending 180 degrees from the main body 303 as the prosthetic valve 300 moves through the funnel segment 214.

Figure 21:
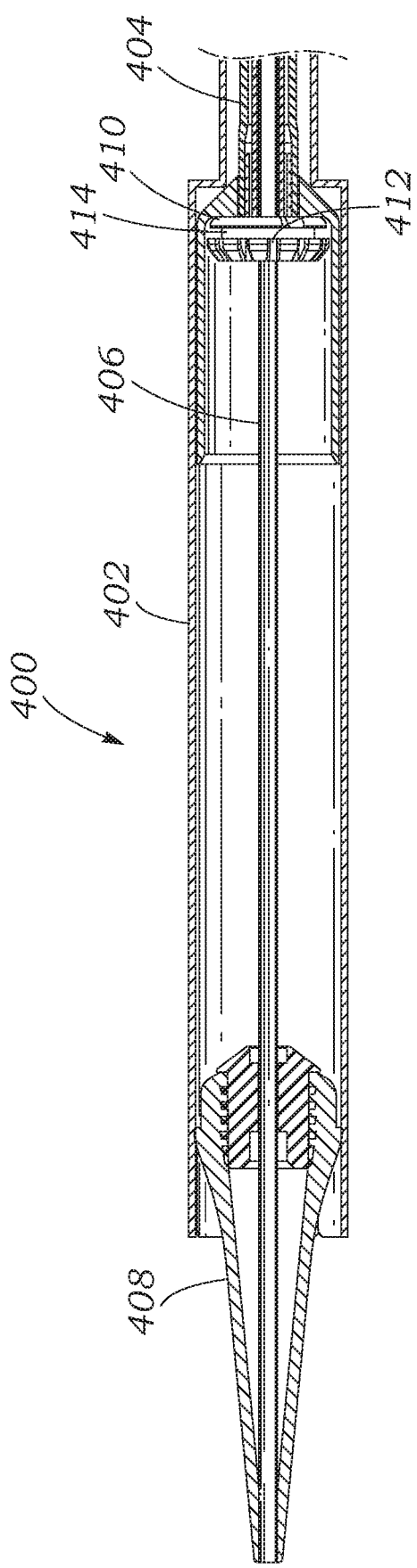
FIG. 21 is a side elevation view of the distal end portion of an exemplary delivery apparatus that can be used to the deliver and implant the prosthetic valve of FIG. 20.

FIG. 21 shows the distal end portion of an exemplary delivery apparatus 400 that can be used to deliver and implant the prosthetic valve 300 in a patient's body. Any of the crimping devices disclosed herein can be used to crimp the prosthetic valve 300 and load it onto the delivery apparatus 400. As shown, the delivery apparatus 400 generally comprises an outer sheath 402, a first shaft 404 extending coaxially through the sheath 402, and a second shaft 406 extending coaxially through the first shaft 404. A nose cone 408 can be attached to the distal end portion of the second shaft 406. Although not shown, the proximal end portions of the sheath 402, the first shaft 404, and the second shaft 406 can be coupled to a handle and each of these components can be moveable axially relative to each other.

A valve-retaining member 410 can be connected to the distal end portion of the first shaft 404 and can include a plurality of circumferentially spaced slots 412 sized to receive the connecting arms 312 of the prosthetic valve 300. During the crimping process, the valve-retaining member 410 initially can be outside of the sheath 402. As the prosthetic valve 300 is initially pushed out of the outlet 212 of the crimping device 200, the connecting arms 312 can be placed within respective slots 412 of the valve-retaining member 410. The enlarged end portions 314 can be positioned within an annular slot 414 proximal to slots 412 to prevent axial separation of the prosthetic valve from the valve-retaining member.

As the prosthetic valve is further advanced from the crimping device, the sheath 402 can be advanced distally over the valve-retaining member 410 and the prosthetic valve 300 so that the prosthetic valve can be delivered and implanted in a patient's body using the delivery apparatus 400. After the delivery apparatus 400 is inserted into a patient's vasculature and the distal end portion is positioned at or adjacent the desired implantation site (e.g., the native mitral valve), the sheath 402 can be retracted proximally to deploy the prosthetic valve 300 from the sheath 402, allowing the prosthetic valve to expand under its own resiliency. When the sheath 402 is retracted proximally beyond the valve-retaining member 410, the connecting arms 312 can expand radially away from their engagement with the slots 412, thereby de-coupling the prosthetic valve from the delivery apparatus.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for crimping a prosthetic valve, the method comprising:
    rotating an actuator of a crimping device relative to a housing and a pusher member of the crimping device, wherein the housing includes a funnel in communication with an outlet of the crimping device and the pusher member extends coaxially through the actuator to abut the prosthetic valve within the housing; and
    engaging the prosthetic valve with the funnel and the pusher member such that at least a portion of the prosthetic valve compresses radially and exits the crimping device via the outlet as the pusher member moves axially through and relative to the housing.

2. The method of claim 1, further comprising advancing the prosthetic valve out of the outlet of the crimping device and into a sheath of a delivery apparatus.

3. The method of claim 1, wherein the pusher member comprises a plurality of ribs extending radially inward toward a longitudinal axis of the crimping device and the method for crimping further comprises aligning at least a portion of a frame of the prosthetic valve within the plurality of ribs.

4. The method of claim 1, wherein the pusher member comprises an annular recess configured to receive a portion of a frame of the prosthetic valve and the method for crimping further comprises positioning the portion of the frame of the prosthetic valve within the annular recess such that the pusher member engages the prosthetic valve.

5. The method of claim 1, wherein rotating the actuator relative to the housing and the pusher member causes the actuator to move axially along a length of the housing.

6. The method of claim 1, further comprising releasably coupling the actuator to the pusher member such that the actuator is rotatably coupled to the pusher member.

7. The method of claim 1, wherein the housing includes one or more longitudinal slots configured to receive one or more external ribs extending longitudinally along an outer surface of the pusher member; the method further comprising:

aligning the housing and pusher member by engaging the external ribs of the pusher member with the slots of the housing.

8. The method of claim 1, wherein the housing comprises two or more housing components, each housing component comprising a portion of the funnel; the method further comprising:
assembling the two or more housing components and placing the housing coaxially around a delivery apparatus prior to crimping of the prosthetic valve.

9. The method of claim 8, further comprising retaining the two or more housing components together with a retaining member configured to encircle and releasably lock the two or more housing components.

10. The method of claim 8, further comprising disassembling the two or more housing components, and removing the two or more housing components from the delivery apparatus.

11. The method of claim 8, wherein assembling the two or more housing components comprises mating one or more recesses of at least one of the housing components to one or more respective protrusions of at least one other of the housing components.

12. A method for crimping a prosthetic valve, the method comprising:
abutting a pusher member of a crimping device against the prosthetic valve at least partially received within a housing of the crimping device, wherein the housing includes an outlet and an internal wall having an inner surface and a plurality of ribs extending radially inwardly from and longitudinally along the inner surface, wherein the ribs are configured to receive the prosthetic valve in a radially expanded state; and
rotating an actuator of the crimping device relative to the housing and the pusher member such that the pusher member moves axially relative to the housing and at least a portion of the prosthetic valve is radially compressed and exits the crimping device via the outlet.

13. The method of claim 12, further comprising positioning the housing, the pusher member, and the actuator coaxially around a shaft of a delivery apparatus.

14. The method of claim 12, wherein the pusher member includes an annular ledge and a plurality of circumferentially spaced fins extending radially from the annular ledge; the method further comprising:
disposing the fins of the pusher member between respective ribs of the housing such that the fins slide between the ribs as the pusher member moves axially relative to the housing.

15. The method of claim 12, wherein the actuator includes an inwardly projection annular ledge and the pusher member includes a lip and a groove; the method further comprising:
deflecting the lip of the pusher member inwardly; and
sliding the annular ledge of the actuator into the groove of the pusher member such that the actuator is releasably and rotatably coupled to the pusher member, and the pusher member extends coaxially through the actuator.

16. The method of claim 12, further comprising rotating the actuator over a length of an outer surface of the housing as the pusher member moves axially through the housing.

17. The method of claim 12, further comprising aligning at least a portion of a frame of the prosthetic valve within the plurality of ribs.

18. The method of claim 12, wherein the pusher member extends coaxially through the actuator.

19. The method of claim 12, the housing further including a proximal end portion, a distal end portion, and a funnel segment along the proximal portion and in communication with the outlet, wherein the internal wall of the housing tapers from the distal portion to the funnel segment and the funnel segment tapers from the internal wall to the outlet.

20. The method of claim 19, wherein the internal wall is tapered at a smaller angle relative to a longitudinal axis of the crimping device than the funnel segment, the method further comprising:
radially compressing the prosthetic valve by a first amount as the prosthetic valve moves along the internal wall of the housing; and
radially compressing the prosthetic valve by a second amount as the prosthetic valve moves along the funnel segment of the housing, wherein the second amount is greater than the first amount.

21. A method for crimping a prosthetic valve, the method comprising:
positioning a housing, a pusher member, and an actuator of the crimping device coaxially around a shaft of a delivery apparatus, wherein the housing includes an outlet and a tapered internal wall terminating at the outlet, the pusher member extends coaxially through the actuator, and the actuator is rotatably coupled to the housing and the pusher member;
rotating the actuator relative to the housing and the pusher member such that the actuator and the pusher member move axially relative to the housing, wherein the actuator rotates over a length of the housing and the pusher member slidably engages the prosthetic valve within the housing; and
pushing the prosthetic valve against the tapered internal wall of the housing such that at least a portion of the prosthetic valve compresses radially and exits the crimping device via the outlet.

* * * * *